United States Patent [19]

Darecchio

[11] 4,397,814

[45] Aug. 9, 1983

[54] APPARATUS FOR PROVIDING OVERRIDING PRESSURE IN HEAT PROCESSING SEALED CONTAINERS

[75] Inventor: Andrea Darecchio, Parma, Italy

[73] Assignee: FMC Corporation, Chicago, Ill.

[21] Appl. No.: 371,855

[22] Filed: Apr. 26, 1982

Related U.S. Application Data

[62] Division of Ser. No. 161,085, Jun. 19, 1980, Pat. No. 4,341,734.

[51] Int. Cl.³ ............................ A61L 2/06; A23L 3/08
[52] U.S. Cl. ...................................... 422/111; 99/468; 99/483; 422/25; 422/27; 422/33; 422/112; 422/298; 422/302
[58] Field of Search .................... 422/111, 112, 25, 27, 422/33, 38, 302, 298; 99/468, 483

[56] References Cited

U.S. PATENT DOCUMENTS

| | | |
|---|---|---|
| 903,853 | 11/1908 | Gartner . |
| 2,733,651 | 2/1950 | Stimpson et al. ............. 99/362 |
| 3,035,886 | 5/1962 | Hickey . |
| 3,093,449 | 6/1963 | Kotarski et al. . |
| 3,404,946 | 10/1968 | Reis . |
| 3,549,312 | 12/1970 | Ernst . |
| 3,598,517 | 8/1971 | Beecher . |
| 3,804,591 | 4/1974 | Bezrodny et al. ............. 422/112 |
| 3,908,031 | 9/1975 | Wistreich et al. ............. 426/335 |
| 3,986,832 | 10/1976 | Smorenburg . |
| 4,066,399 | 1/1978 | Gunther . |
| 4,203,943 | 5/1980 | Gillis et al. ............. 422/111 X |
| 4,282,179 | 8/1981 | Gunther ............. 422/27 |

OTHER PUBLICATIONS

Pickerill, J. K.; "Practical System for Steam-Formaldehyde Sterilizing"; *Lab Practice* (GB), vol. 24, No. 6, Jun. 1975, pp. 401-404.

*Primary Examiner*—Barry S. Richman
*Attorney, Agent, or Firm*—A. J. Moore; H. M. Stanley; R. B. Megley

[57] ABSTRACT

A conventional cooker or retort for heat processing sealed containers, such as sealed pouches, jars or cans, has an evaporator associated therewith. A source of water is coupled to the evaporator through a valve and a source of a liquid having a higher vapor pressure than water, such as ethyl alcohol, is connected to the evaporator through a metering pump. Pressure and temperature within the retort are monitored and signals indicative thereof are connected to controllers for metering the heat supplied to the evaporator and for metering the ethyl alcohol and water delivered to the evaporator. One controller is configured to operate so that as pressure rises, proportions of ethyl alcohol introduced into the evaporator is reduced while the proportion of water introduced is increased. Another controller functions to restrict the amount of heating medium, such as steam, delivered to the evaporator as the retort temperature increases. In this fashion a predetermined pressure and temperature is maintained within the retort such that an overriding pressure is provided relative to the pressure within the sealed containers being processed.

6 Claims, 3 Drawing Figures

APPARATUS FOR PROVIDING OVERRIDING PRESSURE IN HEAT PROCESSING SEALED CONTAINERS

This application is a division, of application Ser. No. 161,085, filed June 19, 1980 now U.S. Pat. No. 4,341,734 issued July 27, 1982.

BACKGROUND OF THE INVENTION

This invention relates to heat processing sealed containers, and more particularly to prevention of container distortion and protection of container seal integrity during heat processing.

Heat sterilization of sealed food containers such as glass jars or flexible pouches generally requires an overriding pressure in the sterilizing environment to keep the containers from rupturing or the container lids from being pushed off due to the usual rise of internal pressure within the containers caused by the processing temperatures. To prevent destruction of the seal integrity it has been necessary to either maintain a positive pressure differential between the interior of the heat processing chamber and the interior of the container or to introduce air together with the heat transfer medium, such as saturated steam, into the processing chamber. The disadvantages associated with maintaining the positive pressure differential relate to system complexity and the disadvantages associated with introducing air with the heating medium to obtain the overriding pressure accrue from a loss of heat transfer efficiency due to the insulating property of the non-condensible gas (air) as well as condensation inefficiencies when the air and steam mixture is passed from the heat processing chamber to a condenser for recovery and return to the system.

U.S. Pat. No. 4,066,399, Gunther, relates to an enclosed sterilizing chamber in which articles to be sterilized are placed. The atmosphere within the chamber is humidified to a predetermined degree prior to introduction of a sterilizing gas. The degree of humidification is obtained by mixing water and an organic solvent in known proportions and atomizing the mixture as it is injected into the chamber. The proper degree of humidification is sensed by a pressure sensor, since relative humidity in the chamber is directly proportional to pressure, and injection of humidifying mixture is stopped. Ethyl alcohol is one organic substance mentioned by Gunther as appropriate for obtaining the desired chamber humidity.

U.S. Pat. No. 3,404,946 issued to Reis discloses apparatus for sterilizing articles within enclosed containers. The containers hold ethyl alcohol which is used as an antiseptic fluid. Steam is introduced into a chamber surrounding the containers to provide a heat source. The pressure of the volatile alcohol in the containers rises faster than the pressure surrounding the containers. The internal container pressure rise presents a danger of container explosion and therefore air pressure is introduced into the chamber to counteract the increased internal container pressure.

U.S. Pat. No. 3,986,382, Smorenburg, also discloses a thermal sterilizing system for filled containers where air is used to provide the overriding pressure to prevent container deformation or rupture.

Kotarski et al. U.S. Pat. No. 3,093,449, also relates to a system wherein steam is used to provide heat at the sterilization temperature in a sterilization chamber and compressed air is introduced into the steam mass to provide an overriding pressure in the chamber for the aforementioned purpose. These patents seem to typify the prior art over which the subject disclosure provides an advance.

SUMMARY OF THE INVENTION

The system for heat processing sealed containers having a first liquid therein includes a sealed heat treatment chamber which is adapted to receive a plurality of containers together with an evaporator which is provided for vaporizing a liquid and for providing the vapors to the sealed chamber at the processing temperature. A pressure sensor is attached to the heat treatment chamber and provides a chamber pressure indicative output. Means is provided for storing a quantity of a second liquid which has a higher vapor pressure than the first liquid. Further means is provided which is responsive to the pressure indicative output and which operates to control the flow of the second liquid between the means for storing the liquid and the evaporator. In this fashion an overriding pressure is provided within the heat processing chamber relative to the pressure within the sealed containers being processed.

The method of heat processing sealed containers having a first liquid contained therein includes the steps of heating a second liquid having a higher vapor pressure than the first liquid to the heat processing temperature. The sealed containers are exposed to the vapors from the heated second liquid so that a positive pressure is maintained on the exterior of the containers relative to the internal pressure of the containers being processed.

Another embodiment of the system for heat processing sealed containers having a first liquid therein includes a sealed heat treatment chamber which is adapted to receive a plurality of containers and an evaporator which is provided for vaporizing a liquid and for providing the vapors to the sealed chamber at the processing temperature. A temperature sensor is attached to the heat treatment chamber and provides a chamber temperature indicative output. Means is provided for storing a quantity of a second liquid which has a higher vapor pressure than the first liquid. Further means is provided which is responsive to the temperature indicative output for controlling the flow of the second liquid between the means for storing and the evaporator. An overriding pressure is thus provided within the heat processing chamber relative to the pressure within the sealed containers being processed.

BRIEF DESCRIPTION OF THE DRAWINGS

FIG. 3 is a chart showing absolute pressure as a function of temperature for a number of different component proportions in a liquid mixture useable in the present invention.

DESCRIPTION OF THE PREFERRED EMBODIMENT

Dalton's law of partial pressure states that in a mixture of gases the molecules of gas of each kind exert a partial pressure which is the same as if that gas was present alone. The total pressure is the sum of the partial pressures exerted by the different gases in the mixture. Consequently, the total pressure within the vapors overlying a liquid mixture of first and second liquids, where the liquid and gaseous phases are in equilibrium, will be higher where the second liquid has a higher vapor pressure (is more volatile) than the total pressure would be over a body of the first liquid alone under the same conditions. This principle is found to be useful in heat processing sealed containers where a positive pressure must be maintained on the exterior of the containers relative to the container interior pressure. Specifically, where steam is used as the heat transfer agent, the vapors from a liquid having a higher vapor pressure than water may be mixed with the steam so that the total pressure of the vapor mixture is greater than the pressure which would be exerted by the water vapor (steam) alone. It should be noted that hereinafter the preferred embodiment will be described in terms of a mixture of water with a liquid having a higher vapor pressure than water to thereby obtain a vapor phase exerting a higher pressure than would be exerted by the water vapor alone. Nonetheless, the invention is not limited to the use of mixtures of water with a higher vapor pressure liquid, but may utilize a liquid which itself has a higher vapor pressure than a liquid within any of the sealed containers. The invention may also utilize a mixture of two or more liquids wherein the total pressure exerted by the combined vapors is greater than the total pressure exerted by the combined vapors from the liquid within the second containers.

Figure 2:
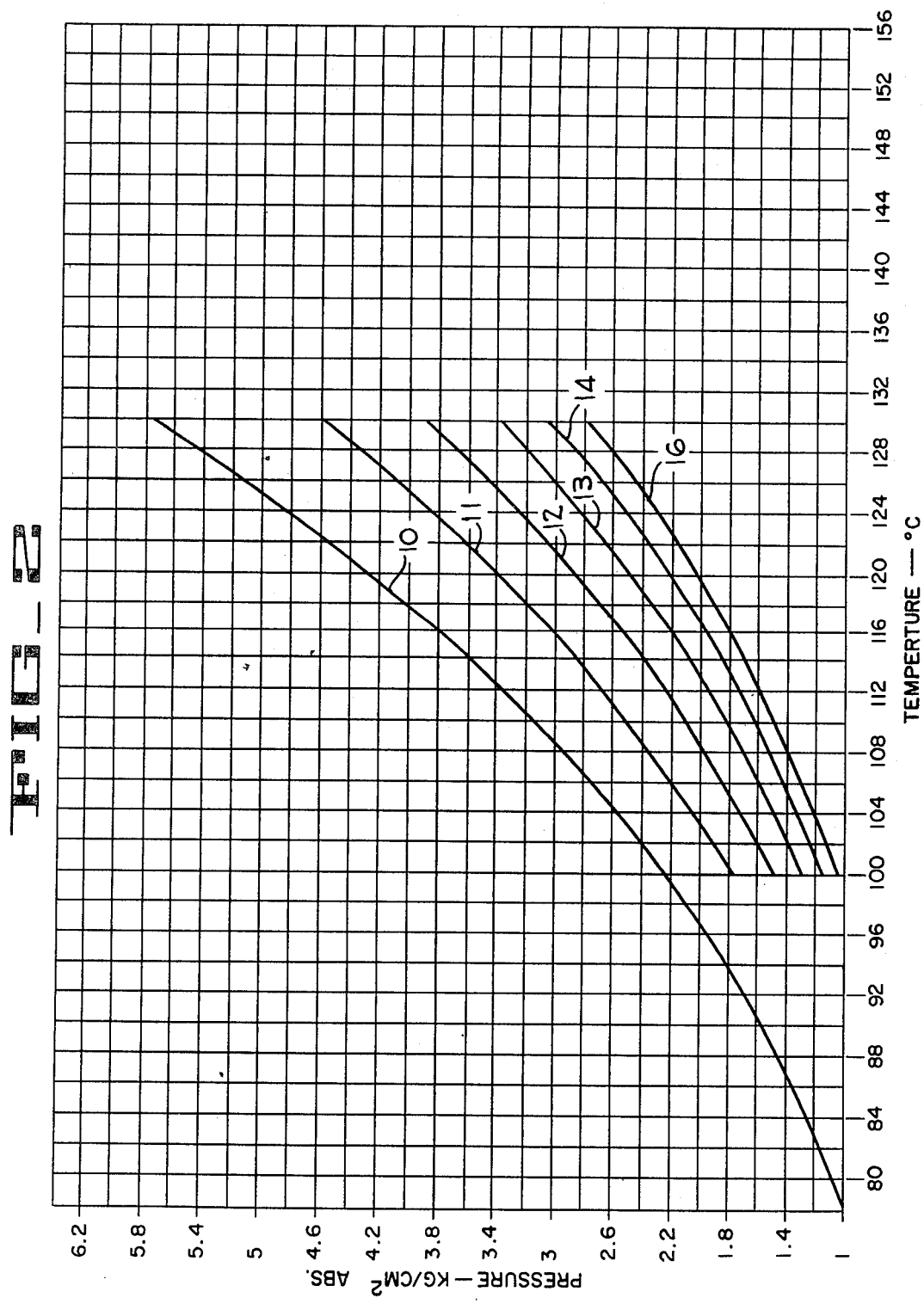
FIG. 2 is a chart showing absolute pressure as a function of temperature for a number of different component proportions in vapor mixtures which may be used in the present invention.
Figure 7:
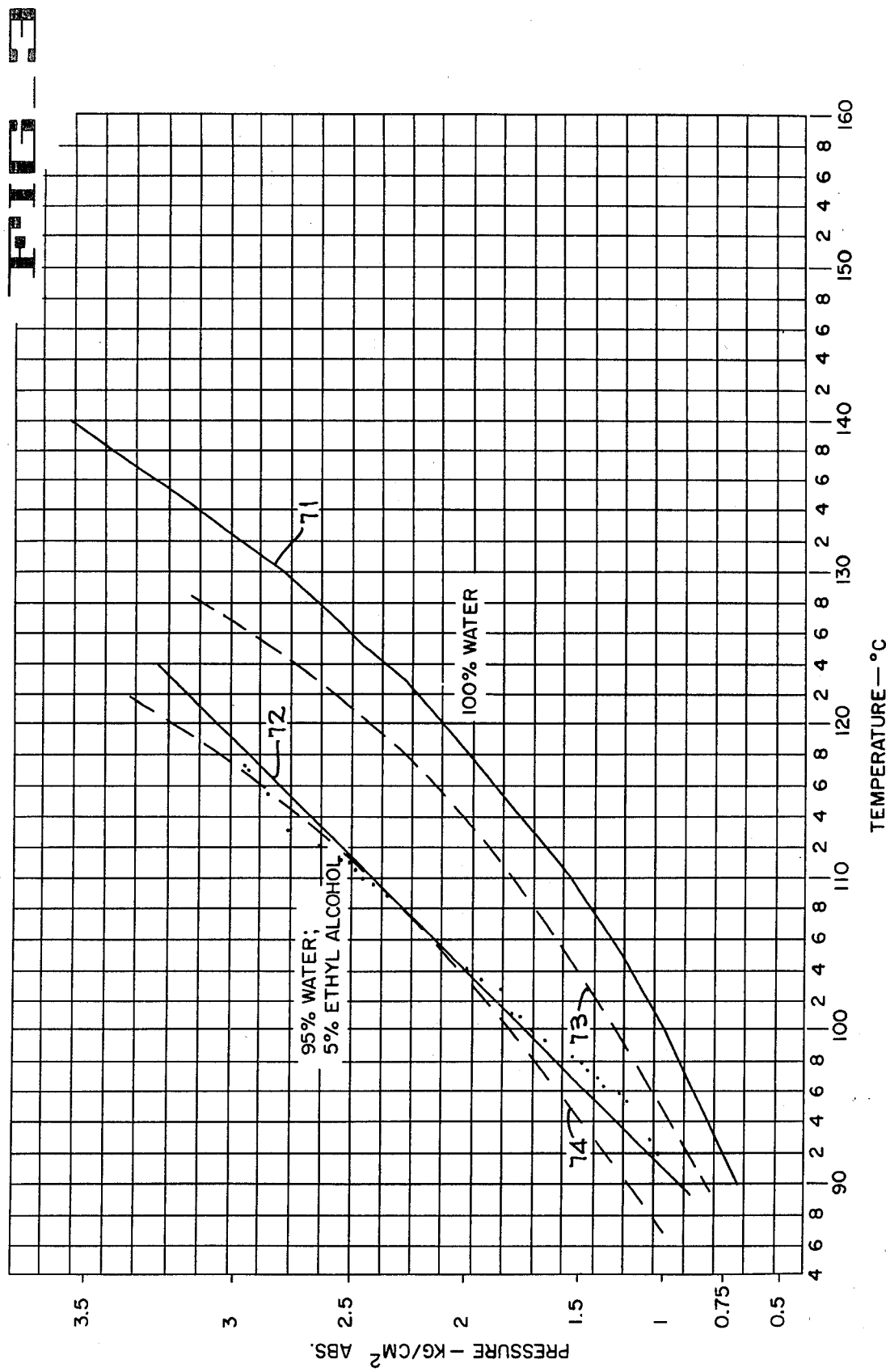

By way of illustration of the foregoing principle using specific substances in vapor phase, FIG. 2 shows a family of curves wherein pressure in kilograms per square centimeter absolute is shown as a function of temperature. Curve 10 shows the relationship wherein the vapors are 100% ethyl alcohol. Curve 11 shows the relationship for vapors which are 20% water and 80% ethyl alcohol. Curve 12 is for vapors 40% water, 60% ethyl alcohol; curve 13, 60% water, 40% ethyl alcohol; curve 14, 80% water, 20% ethyl alcohol; and curve 16 shows the relationship of pressure to temperature for the vapors which are 100% water. This family of curves shows that when the proportion of ethyl alcohol vapors within the vapor mass increases, at a given temperature, the total pressure within the vapor mass increases. Ethyl alcohol is a mono-alcohol having a vapor pressure of 0.29 kg/cm$^2$ at 20° C. This may be seen to be higher than the vapor pressure of 0.12 kg/cm$^2$ at the same temperature for water. For the purposes of this description the temperature range of interest will be such as to assure that the liquid described as having a higher vapor pressure characteristic maintains such characteristic throughout the temperature range.

The system of the present invention includes a conventional "cooker" or retort 17 which has a "can lock" 18 well known to those of skill in this art. The "can lock" operates to pass a plurality of sealed containers 19 into and out of the retort 17 without venting the interior of the retort to the surrounding atmosphere.

Figure 1:
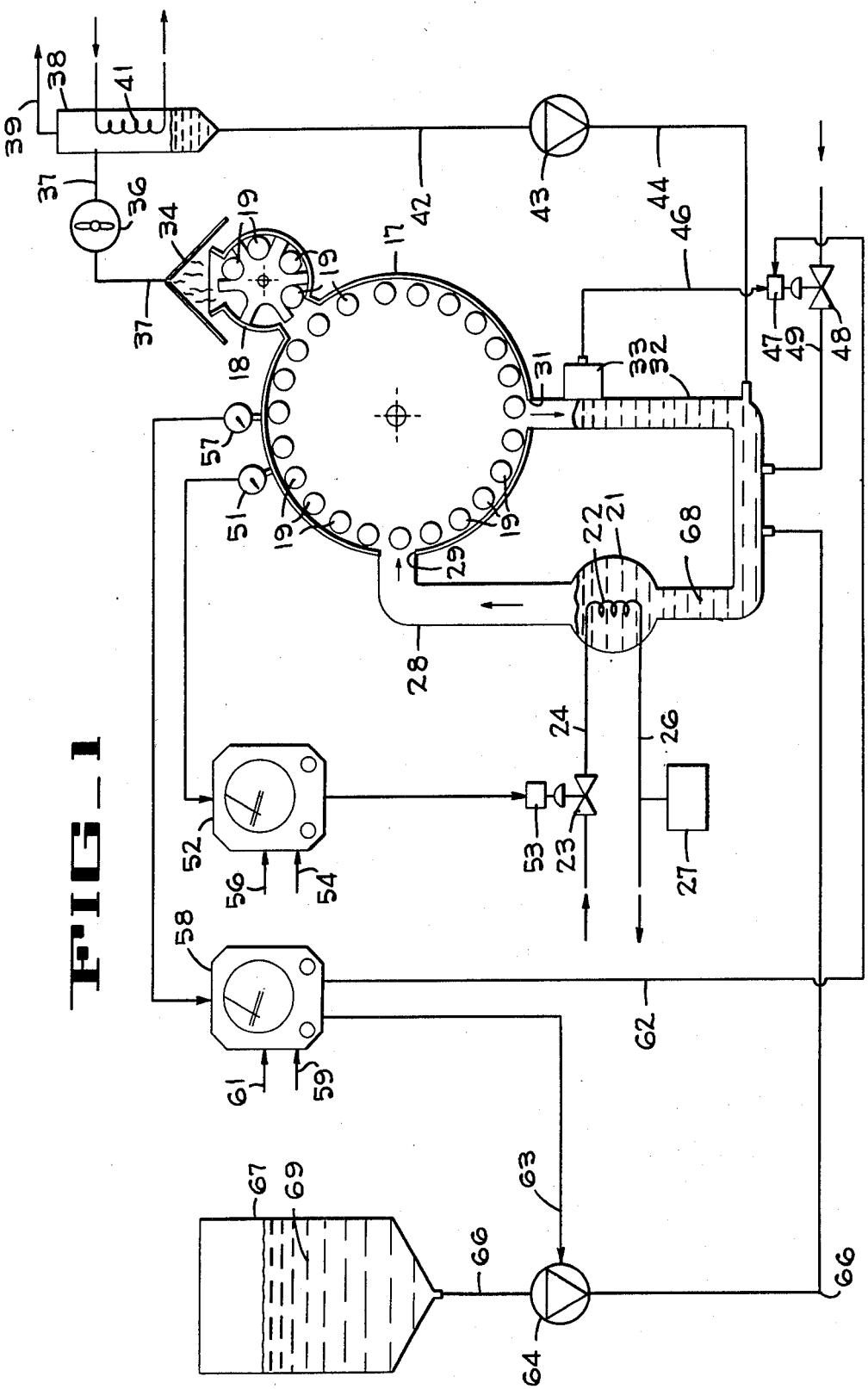
FIG. 1 is a mechanical schematic drawing of the system incorporating the present invention.

An evaporator 21 defines a chamber therewithin in which a heating coil 22 is disposed (FIG. 1). The coil 22 conducts a heating medium such as steam. A control valve 23, such as an air operated diaphragm valve, is disposed in a line 24 leading from a steam source (not shown) to one end of the heating coil 22. A return line 26 is coupled to the other end of the heating coil 22 to conduct the heating medium away from the evaporator after heat has been transferred thereto. A water condensate trap 27 is coupled to the return line 26 in a conventional manner. A conduit 28 connects the chamber in the evaporator 21 to the interior of the retort 17 through a side port 29 in the retort. A bottom port 31 in the retort 17 passes condensation from the retort to a conduit 32 from which it is returned to the chamber in the evaporator 21. A level control 33 is disposed in the conduit 32 which senses the liquid level within the conduit 32 and therefore within the evaporator 21 as shown.

Vapors escaping from the retort 17 through the can lock 18 are collected by means such as a hood 34 and conducted through a line 37 by a fan 36 to a condenser 38. Non-condensible gas such as air which enters the hood 34 is exhausted from the condenser 38 through an exhaust line 39 while condensible gases are cooled to a liquid state by contact with a cooling coil 41 which carries a cooling medium therethrough. The condensate from the condenser 38 is delivered through a line 42 to a condensate pump 43 from which it is returned to conduit 32 and the evaporator 21 through a line 44.

The level sensor 33 provides an output signal which is connected through a conductor 46 to an air operated diaphragm valve control 47. The control 47 operates to open and close an air operated diaphragm valve 48 disposed in a line 49 which conducts water from a water source to the conduit 32 and the evaporator 21.

A temperature sensor 51 is coupled to the retort 17 to sense the internal temperature of the retort. The temperature sensor provides a temperature indicative signal which is connected to a temperature controller 52. The controller 52 provides an output which is coupled to another air operated diaphragm valve control 53 operating in conjunction with diaphragm valve 23. Compressed air from an air supply is connected to the temperature controller 52 through a line 54. The compressed air is used to operate the diaphragm valve control 53. A temperature set point is impressed on the controller 52 by any conventional means such as a potentiometer adjustment and is shown in FIG. 1 coupled to the temperature control through a connection 56. A pressure sensor 57 is also coupled to the retort 17 and provides an output signal indicative of pressure within the retort. The pressure indicative signal is connected to a pressure controller 58 having a compressed air supply line 59 and a pressure set point connection 61 associated therewith similar to those described for the temperature controller 52. Pressure controller 58 has an air outlet line 62 connected thereto which extends to the diaphragm valve control 47 for the valve 48. The pressure controller also has an air outlet line 63 extending to a metering pump 64 located in a liquid line 66 which is connected to the conduit 32 and the chamber within the evaporator 21. The liquid line 66 extends from the pump 64 to a fluid reservoir 67.

The manner in which the apparatus of FIG. 1 operates to perform the process of the present invention is set forth as follows. The sealed containers 19 are placed into the retort 17 through the container lock 18. The containers 19 generally have a volatile liquid therein such as some aqueous solution and also usually contain some air (referred to as "head-space gas"). Heat processing of the containers 19, for example to sterilize the contents of the containers, causes vaporization in some of the aqueous solution within the containers plus a rise in pressure due to heating of the "head-space gas." A resultant rise in the internal container pressure occurs which if not counteracted will tend to deform or actually rupture the containers. Therefore, a liquid 68 is introduced into the chamber within the evaporator 21 which has a higher vapor pressure than the vapor pressure of the aqueous solution within the containers 19. The liquid 68 is heated by conducting a heating medium through the coil 22 immersed in the liquid 68 until the liquid 68 and the vapors thereabove are heated to the desired processing temperature. The vapors overlying the surface of the liquid 68 are directed through the conduit 28 and the side port 29 into the retort 17 where they engulf the sealed containers 19. As may be seen by reference to FIG. 2 of the drawings, vapors overlying a body of liquid having a component liquid therein with a relatively high vapor pressure will exert a relatively high pressure on the surfaces confining the vapors. Thus, a positive pressure is maintained on the exterior of the containers 19 relative to the internal pressure of the containers for the temperature range of interest.

In the interests of explaining the details of the operation of the system shown in FIG. 1 a preferred embodiment includes a volume of ethyl alcohol 69 disposed within the reservoir 67. A water supply is connected to the input side of the diaphragm valve 48. Sealed containers 19 are received by the retort 17 through the container lock 18 and a mixture of ethyl alcohol 69 and water is introduced into the conduit 32 and the chamber within the evaporator 21 through the metering pump 64 and the liquid line 66 as well as the diaphragm valve 48 and the liquid line 49. The level of the liquid mixture introduced is controlled by the level sensor 33 which shuts off the influx of water by controlling the diaphragm valve 48 to a closed position with the valve control 47. Since initially pressure and temperature are likely to be below operating pressure and temperature, steam or some other heating medium is introduced through the open diaphragm valve 23 into the heating coil 22 within the evaporator 21. As the mixture of ethyl alcohol and water within the evaporator 21 is heated, the vapor pressure above the liquid mixture increases with temperature at a rate which is faster than the rate of increase which would occur within a mass of water vapor alone above a body of water. The higher rate is due to the higher vapor pressure characteristic of the ethyl alcohol within the liquid mixture 68.

As the temperature rises, the temperature sensor 51 produces the temperature indicative signal which is connected to the temperature controller 52. When the temperature reaches the point corresponding to the temperature set point as imposed on the controller through the line 56, air is introduced through the controller from the input line 54 to the valve control 53 to close off the diaphragm valve 23 and thereby limit the flow of heating medium through the coil 22 in the evaporator 21. Thus, as the temperature rises within the retort 17 the temperature controller 52, through the valve control 53, tends to close the diaphragm valve 23.

As described hereinbefore, a rise in temperature under these conditions produces a rise in pressure within the retort 17. Pressure sensor 57 produces a pressure indicative signal connected to the pressure controller 58. As the pressure set point which is coupled to the pressure controller through the line 61 is approached, air is passed from the air inlet line 59 through the line 62 which causes the valve controller 47 to open the diaphragm valve 48 and thus introduce water through the line 49 into the mixture 68. Concurrently air is introduced through the line 63 by the pressure controller to reduce the flow of ethyl alcohol from the reservoir 67 through the metering pump 64 and the liquid line 66 to the mixture 68 within the evaporator 21. Since the temperature and pressure within a volume of gas vary directly, the temperature could, be sensed instead of the pressure and a temperature controller could be used to indirectly affect the flow of alcohol from the reservoir 68 and/or directly affect the flow of water through the diaphragm valve 48. It may therefore be seen that a stable system is provided wherein as temperature rises the heat energy provided to the evaporator 21 through the coil 22 to vaporize the mixture 68 is decreased. Dependent upon the particular characteristics of the pressure controller utilized, it may also be seen that as pressure rises either additional water is introduced into the liquid mixture 68 or less ethyl alcohol is introduced into the mixture, or both, as controlled by the pressure controller 58.

Since vapors containing ethyl alcohol are desireably prevented from entering areas where persons may inhale them and be adversely affected, any mixture of ethyl alcohol and water vapors escaping from the entry and exit point (can lock 18) for sealed containers at the retort is collected and contained by the collection hood 34 as described hereinbefore. It is essential to prevent noncondensible gases from entering the system because such gases tend to collect about structure where heat transfer is desirable and to provide an insulating layer thereabout, thus obstructing the desired heat transfer. This may adversely affect heat transfer between the heating medium (vapor phase above liquid mixture 68) and the sealed containers 19 within the retort 17 or it may occur around the coil 41 within the condenser 38. Thus, any air introduced into the vapors collected by the hood 34 is exhausted from the condenser 38 by the air exhaust line 39 while the remainder of the vapors are condensed by contact with the cooling surface of the coil 41 and collected in the bottom of the condenser 38. The condensate is then delivered through the line 42 to the condensate pump 43 from which it is pumped back to the body of liquid 68 within the evaporator 21 through the line 44.

With reference to FIG. 3 of the drawings, the pressure above a body of liquid in kilograms per square centimeter absolute is shown as a function of temperature in degrees Centigrade. While the chart of FIG. 2 shows pressure as a function of temperature for a body of vapor having the stipulated percentage composition of ethyl alcohol and water in the vapor phase, the chart of FIG. 3 shows pressure as a function of temperature over a body of liquid having the stipulated percentage compositions in the liquid phase. Curve 71 of FIG. 3 shows the absolute pressure above a body of liquid consisting of 100% water when the vapor and liquid phases are in equilibrium at a given temperature. Curve 72, on the other hand, is shown drawn through a group of experimentally obtained points and approximates a straight line through the points. The experimental data which resulted in the curve 72 was obtained with a liquid mixture 68 consisting of 95% water and 5% ethyl alcohol by weight. The dashed curve 73 of FIG. 3 shows the theoretical relationship between pressure and temperature for a 95-5% water and ethyl alcohol mixture by weight. While the inventor is unable to explain the showing by curve 72 of a marked increase in pressure overlying the 95% water, 5% ethyl alcohol mixture for a given temperature compared to the theoretical curve 73, the experimental data shows the tendency for the apparatus and method disclosed herein to provide overriding pressure as compared to the pressure existing over a body of pure water at various temperatures.

As is apparent from a comparison of FIGS. 2 and 3 the percent of ethyl alcohol vapor within the total vapor mass overlying a mixture of ethyl alcohol and water is considerably larger than the percent by weight of ethyl alcohol in the liquid mixture. For example, a liquid mixture containing 5% ethyl alcohol by weight and 95% water will provide a pressure of three atmospheres at 126.7° C. wherein the vapor mass contains 41.8% ethyl alcohol vapors. On the other hand, a liquid mixture containing 20% ethyl alcohol by weight and 80% water will provide three atmospheres pressure at 117.7° C. wherein the vapor phase consists of 64.8% ethyl alcohol vapors. A theoretical relationship obtained from engineering charts showing pressure as a function of temperature above a liquid mixture of 20% ethyl alcohol by weight and 60% water is shown as curve 74 in FIG. 3 of the drawings. The described invention is deemed to provide its primary utility when the ethyl alcohol content of the liquid mixture 68 is within the range of 5–20% by weight. It should further be noted that any monoalcohol may be used for the liquid having a relatively high vapor pressure. Other relatively high vapor pressure liquids which are miscible with water may be used in obtaining an overriding pressure within the retort.

Although the best modes contemplated for carrying out the present invention have been herein shown and described, it will be apparent that modification and variation may be made without departing from what is regarded to be the subject matter of the invention.

What is claimed is:

1. A system for heat processing sealed containers having a head-space and first liquid therein which vaporizes during processing, the containers being of the type capable of maintaining an internal pressure that is different than the pressure acting on the exterior of the containers, comprising;
   a sealed heat treatment chamber adapted to receive a plurality of containers,
   an evaporator for heating and vaporizing a processing liquid for providing the vapors to the sealed chamber at the processing temperature,
   control means including a pressure sensor communicating with the heat treatment chamber for providing a pressure indicative output,
   means for storing a quantity of a second liquid having a higher vapor pressure than the first liquid, and
   means responsive to said pressure indicative output for controlling the flow of said second liquid between said means for storing and the evaporator for changing the proportion of the second liquid in the processing liquid so that a higher overriding pressure is provided in the treatment chamber than the pressure generated within the sealed containers.

2. A system as in claim 1 wherein the processing liquid includes water, and further comprising conduit means for providing makeup water to said evaporator, means for controlling the flow of makeup water to the evaporator, said last named means being responsive to said pressure indicative output so that the proportion of water mixed into said processing liquid is increased when higher overriding pressures are sensed, said processing liquid being a mixture of mono-alcohol and water containing from 5–20% alcohol by weight.

3. A system for heat processing sealed containers having a head-space and a first liquid therein which vaporizes during processing, the containers being of the type capable of maintaining an internal pressure that is different than the pressure acting on the exterior of the containers, comprising:
   a sealed heat treatment chamber adapted to receive a plurality of containers,
   an evaporator for vaporizing a processing liquid and for providing the vapors to the sealed chamber at the processing temperature,
   control means including a temperature sensor communicating with the heat treatment chamber for providing a temperature indicative output,
   control means including a pressure sensor communicating with a heat treatment chamber for providing a pressure indicative output,
   means for storing a quantity of a second liquid having a vapor pressure higher than the first liquid,
   means responsive to said pressure indicative output for controlling the flow of said second liquid between said means for storing and the evaporator, and
   means responsive to said temperature indicative output for controlling heat applied to said processing liquid at the evaporator for maintaining the processing temperature constant and for providing a pressure that is greater within the heat treatment chamber than the pressure within the sealed containers.

4. A system as in claim 3 wherein the processing liquid includes water, further comprising conduit means for providing makeup water to said evaporator, means for controlling the flow of makeup water to the evaporator, said last named means being directly responsive to said pressure indicative output for limiting the overriding pressure, said processing liquid comprising a mixture of mono-alcohol and water containing 5–20% alcohol by weight.

5. A system for heat processing sealed containers having a head-space and a first liquid therein which vaporizes during processing, the containers being of the type capable of maintaining an internal pressure that is different than the pressure acting on the exterior of the containers, comprising;
   a sealed heat treatment chamber adapted to receive a plurality of the containers,
   an evaporator for vaporizing a processing liquid and for providing the vapors to the sealed chamber at the processing temperature,
   control means including a temperature sensor communicating with the heat treatment chamber for providing a temperature indicative output,
   means for storing a quantity of a second liquid having a higher vapor pressure than the first liquid, and
   means responsive to said temperature indicative output for controlling the flow of said second liquid between said means for storing and the evaporator so that an overriding pressure is provided in the treatment chamber that is higher than the pressure generated within the sealed containers.

6. A system as in claim 5 wherein the processing liquid includes water, further comprising conduit means connecting said evaporator to a makeup water supply, means for controlling the flow of makeup water to the evaporator, said last named means being responsive to said temperature indicative output so that the proportion of water mixed into said second liquid is decreased when higher temperatures are sensed, said processing liquid being a mixture of mono-alcohol and water containing from 5–20% alcohol by weight.

* * * * *